United States Patent [19]
Kasat et al.

[11] Patent Number: 5,490,979
[45] Date of Patent: Feb. 13, 1996

[54] CLEAR ANTIPERSPIRANT STICK GELLED WITH DIBENZYLIDENE SORBITOL AND CONTAINING A GUANIDINE COMPOUND AS GEL STABILIZER, AND PROCESS OF MAKING SAME

[75] Inventors: Radhakrishna B. Kasat, Bellemead; Wilson Lee, Bloomfield; David R. McCarthy, Basking Ridge; Norayr G. Telyan, North Caldwell, all of N.J.

[73] Assignee: The Mennen Company, Morristown, N.J.

[21] Appl. No.: 178,823

[22] Filed: Jan. 7, 1994

[51] Int. Cl.⁶ .................. A61K 7/32; A61K 7/34; A61K 7/36; A61K 7/38

[52] U.S. Cl. .............. 424/66; 424/DIG. 5; 424/67; 424/68

[58] Field of Search .......................... 424/66, 68

[56] References Cited

U.S. PATENT DOCUMENTS

| | | | |
|---|---|---|---|
| 3,152,181 | 10/1964 | Shapiro et al. | 424/66 |
| 3,769,427 | 10/1973 | Hughes et al. | 424/47 |
| 3,934,004 | 1/1976 | Orren | 424/68 |
| 4,246,285 | 1/1981 | Van Duzee | 424/47 |
| 4,252,789 | 2/1981 | Broad | 424/65 |
| 4,390,033 | 6/1983 | Khalil et al. | 424/70 |
| 4,518,582 | 5/1985 | Schamper et al. | 424/66 |
| 4,719,102 | 1/1988 | Randhawa et al. | 424/68 |
| 4,772,835 | 2/1988 | Schamper et al. | 424/66 |
| 4,774,079 | 9/1988 | Shin et al. | 424/66 |
| 5,171,565 | 12/1992 | Akhtar et al. | 424/71 |
| 5,200,174 | 4/1993 | Gardlik et al. | 424/66 |
| 5,258,174 | 11/1993 | Sehebece | 424/68 |
| 5,270,034 | 12/1993 | Cheng | 424/68 |
| 5,376,363 | 12/1994 | Benfatto et al. | 424/66 |
| 5,378,452 | 1/1995 | Greczyn | 424/66 |
| 5,405,605 | 4/1995 | Shin | 424/66 |

FOREIGN PATENT DOCUMENTS

| | | | |
|---|---|---|---|
| 0318206 | 5/1989 | European Pat. Off. . | |
| 0404533 | 12/1990 | European Pat. Off. . | |
| 0404532 | 12/1990 | European Pat. Off. . | |
| 0451002A2 | 3/1991 | European Pat. Off. | 424/66 |
| 0512770 | 5/1992 | European Pat. Off. | 424/68 |
| 2310800 | 12/1976 | France . | |
| WO92/19221 | 4/1992 | WIPO | 424/66 |

*Primary Examiner*—Dale R. Ore
*Attorney, Agent, or Firm*—Antonelli, Terry, Stout & Kraus

[57] ABSTRACT

Disclosed is a clear, antiperspirant material-containing, gel stick composition, containing an acidic antiperspirant material (e.g., an aluminum salt) and gelled with dibenzylidene sorbitol, the composition including a guanidine compound (for example, guanidine carbonate or aminoguanidine bicarbonate) as a stabilizing agent to reduce degradation of the gel and of the dibenzylidene sorbitol gelling agent. Also disclosed are continuous processes for forming the gel stick composition, wherein degradation of the dibenzylidene sorbitol gelling agent in the presence of the antiperspirant material is reduced.

40 Claims, 2 Drawing Sheets

CLEAR ANTIPERSPIRANT STICK GELLED WITH DIBENZYLIDENE SORBITOL AND CONTAINING A GUANIDINE COMPOUND AS GEL STABILIZER, AND PROCESS OF MAKING SAME

BACKGROUND OF THE INVENTION

The present invention relates to antiperspirant material-containing, solid gel stick compositions, and methods of making such compositions. In particular, the present invention is directed to clear, antiperspirant material-containing solid gel stick compositions, gelled by dibenzylidene sorbitol, and methods of making such stick compositions. More particularly, the present invention is directed to a clear antiperspirant solid gel stick composition containing an acidic antiperspirant active agent (for example, an acidic astringent metallic salt, such as an astringent aluminum salt) in the presence of dibenzylidene sorbitol as a gelling agent, the composition being stable, over extended periods of time, against deterioration of the gel (and being stable against deterioration of the gelling agent), and methods of making the same.

While dibenzylidene sorbitols are stable in alkaline or neutral media, such compounds are not stable in acidic media. In an acidic environment, such as in the presence of acidic antiperspirant materials, and when in the presence of even small amounts of water, the dibenzylidene sorbitol deteriorates and breaks down. Accordingly, there is a need to find a way to stabilize the sticks containing acidic antiperspirant material, and gelled with dibenzylidene sorbitol, against such deterioration.

U.S. Pat. No. 4,518,582 to Schamper, et al discloses an antiperspirant stick composition containing dibenzyl monosorbitol acetal in the presence of acidic antiperspirant-active salts, which composition is stable for extended periods of time at elevated temperatures. The composition contains at least a reactive solvent (such as water, methanol, ethanol, n-propanol, ethylene glycol, 1,2-propylene glycol, 1,3-propylene glycol, etc.), dibenzyl monosorbitol acetal, an antiperspirant-active compound, and a gel stabilizer, the gel stabilizer being a member of a group consisting of magnesium sulphate, zinc acetate and hexamethylenetetramine and mixtures thereof. This patent discloses that the stabilizer prevents or retards deterioration of the gelled sticks, especially when exposed to elevated temperatures.

Another patent disclosing stabilizers for solid gel antiperspirant sticks containing an acidic antiperspirant-active compound in the presence of dibenzyl monosorbitol acetal is U.S. Pat. No. 4,719,102 to Randhawa, et al. This patent discloses that the sticks include a solvent which is a small, polar organic compound (suitable compounds fitting within this class being cyclic esters, amides, amines, ketones, ureas, carbamates, sulfoxides and sulfones, and their open chain analogs); a cosolvent (such as primary or low molecular weight alcohols, including ethanol, n-propanol, 1,2-propylene glycol, diethylene glycol, etc., and mixtures thereof); dibenzyl monosorbitol acetal; an antiperspirant-active compound; and a gel stabilizer, the gel stabilizer being a member of a group consisting of N-(2-hydroxyethyl) fatty ($C_8$–$C_{20}$) acid amides, magnesium sulfate, zinc acetate, acetamide monoethanol amine and hexamethylenetetramine, and mixtures thereof.

U.S. Pat. No. 4,722,835 to Schamper, et al also discloses antiperspirant gel stick compositions gelled with dibenzyl monosorbitol acetal and containing an acidic antiperspirant compound, and also containing a stabilizer for the gel. This patent teaches that the compositions include a solvent which is a small, polar organic compound, as discussed previously in connection with U.S. Pat. No. 4,719,102; dibenzyl monosorbitol acetal; an antiperspirant-active compound; and the gel stabilizer, such gel stabilizer being a basic metallic salt (such as zinc oxide, calcium acetate, magnesium oxide, calcium carbonate, calcium hydroxide, magnesium carbonate, sodium carbonate, zinc carbonate and potassium carbonate). This patent discloses that these basic metallic salt gel stabilizers can stabilize the gel, even at high temperatures, even when propylene carbonate or butyrolactone are used as solvents.

Other patent documents disclosing antiperspirant sticks gelled with a dibenzylidene sorbitol and including stabilizers for the gel are European Patent Application (EPA) No. 451,002A2; European Patent Application (EPA) No. 512,770A1; and World Intellectual Property Organization International Published Application (PCT) No. WO92/19221.

EPA No. 451,002A2 discloses a stable, substantially anhydrous and substantially lower monohydric alcohol free, transparent, gelled, antiperspirant composition gelled by dibenzylidene monosorbitol acetal, containing acidic antiperspirants, and utilizing dihydric alcohols containing 3 to 6 carbon atoms as solvents, with the acetal being stabilized against hydrolysis and the formation of benzaldehyde by the presence of a stabilizing amount of a selected organic base, the organic base being a weakly basic, nitrogen-containing, organic compound. Preferred organic bases are urea; imidazole; 2-amino-2-hydroxymethyl-1,3-propanediol (Tris buffer); 2-amino-2-methyl-1-propanol; and N, N-tetrakis-2-hydroxypropyl ethylene diamine. This patent document discloses that strong bases which form compositions having a pH higher than 5 tend to precipitate the antiperspirant when attempts are made to employ them in the preparation of transparent antiperspirant sticks. The contents of EPA No. 451,002A2 are incorporated herein by reference in their entirety.

EPA No. 512,770A1 discloses a stable, substantially anhydrous and substantially lower aliphatic monohydroxy alcohol free cosmetic composition gelled by dibenzylidene monosorbitol acetal, and containing acidic antiperspirant compounds and utilizing dihydroxy aliphatic alcohols containing 3–6 carbon atoms as solvents, wherein the dibenzylidene monosorbitol acetal gelling agent is stabilized against hydrolysis and the formation of benzaldehyde by the presence of a stabilizing amount of a selected inorganic base, the inorganic base including alkali and alkaline earth metal oxides, hydroxides, carbonates or bicarbonates, and trivalent metallic hydroxides. Specific inorganic bases include sodium and potassium hydroxides, carbonates and bicarbonates as well as calcium and magnesium oxides, hydroxides and carbonates, aluminum hydroxide and aluminum magnesium hydroxide (provided these bases are soluble in the composition). This patent document further discloses that the decomposition of the gelling agent to benzaldehyde, which imparts an undesirable odor or color, may be further inhibited by adding a compound which will react with the benzaldehyde to produce a colorless and substantially odorless product. Such benzaldehyde scavenger includes polyhydroxy aliphatic polyhydric alcohols, such as glycerin.

PCT No. WO92/19221 discloses solid antiperspirant compositions in gel stick form, having an acid pH, and including (1) an antiperspirant active; (2) a gelling agent selected from the group consisting of substituted and unsubstituted dibenzylidene alditols; (3) a solvent for the gelling agent, preferably including a solvent material selected from the group consisting of monohydric and polyhydric alcohols, and mixtures thereof; and (4) a gelling agent stabilizer, the stabilizer being a basic metallic salt of an acid having a pKa of from about 3.8 to about 6.5 at 25° C., the salt being at least partially soluble in the composition and being selected from the group consisting of $C_4$–$C_6$ dicarboxylate salts, $C_6$–$C_8$ monocarboxylate salts, and substituted or unsubstituted benzoate salts, and Mixtures thereof, the gelling agent stabilizer not containing amino or amido functionalities. This patent document teaches that for clear or translucent sticks, the gelling agent stabilizer present in the composition should be fully soluble in the composition, in order to minimize refraction of light.

The foregoing patent documents also disclose methods for forming the disclosed antiperspirant stick compositions containing the antiperspirant materials and gelling agent. In particular, attention is directed to U.S. Pat. Nos. 4,719,102 and 4,722,835. Each of these patents discloses processes of forming the stick compositions, including dissolving the antiperspirant active in one phase and the dibenzyl monosorbitol acetal gellant in another phase. The two phases are then combined and poured into a mold or into the final package. The other components are added to either of the two phases depending on the compatibility of the component with the phases. More phases can be utilized, if desired, by forming a separate solution of some of the components, with the separate phases then being added to either of the two main phases; or all of the phases could be poured together at the end, as, for example, with a multi-stream filling head or an in-line mixer.

PCT No. WO92/19221 discloses a process of forming an antiperspirant gel stick, including preparing a solution containing the gelling agent, a solvent for the gelling agent, and the gelling agent stabilizer; mixing an antiperspirant active into such solution; and cooling the solution to form a gel.

While, as seen in the foregoing, there has been a great deal of development work into forming antiperspirant sticks, including clear antiperspirant gel sticks, containing acidic antiperspirant active ingredients and gelled with a dibenzylidene sorbitol, it is still desired to provide a clear stick composition containing an acidic antiperspirant active ingredient and gelled with dibenzylidene sorbitol, which has increased stability over extended periods of times and wherein deterioration of the gelling agent, and production of benzaldehyde and formaldehydes due to such deterioration, are reduced. It is also still desired to provide such clear antiperspirant sticks wherein manufacture of the sticks is simplified.

U.S. Pat. No. 3,934,004 to Orren discloses antiperspirant compositions for topical application, containing selected reducing agents to prevent the formation of stains in soiled garments. This patent discloses that the stain resulting from the use of aluminum salt antiperspirant compositions can be reduced by either incorporating into the antiperspirant composition, or by applying to the affected areas of the garments immediately prior to washing of the garments, specified reducing agents which act to prevent the development of an antiperspirant yellow stain during subsequent cleaning of the garments. This patent discloses that the useful reducing agents include both organic and inorganic reducing agents which are water soluble (or water dispersible) and are cosmetically acceptable (that is, they are non-staining, non-irritating to the skin, and essentially odorless). Suitable reducing agents having these properties include a number of organic and inorganic sulphur-or phosphorous-containing compounds, as well as a number of stannous or titanous salts which may be either organic or inorganic. Suitable inorganic sulphur-containing reducing agents include various sulfites, bisulfites, hydrosulfites, metabisulfites, and thiosulfates. Useful organic sulphur-containing reducing agents include organic salts, such as organic bisulfites, in which the bisulfite group has replaced the hydrogen atom of an amino group, including monoethanolamine bisulfite, urea bisulfite, guanidine bisulfite, ethylaminebisulfite, and ethylenediamine bisulfite as well as higher linear and branched chain homologs and polymers thereof; and adducts of sulphur dioxide which are addition products formed between low molecular weight aldehydes or ketones and sodium or zinc bisulfite. This patent goes on to state that the antiperspirant compositions may be prepared in known forms such as emulsions, suspensions, creams, lotions and the like; and that these compositions also contain the usual auxiliary ingredients such as fillers, perfumes and surfactants.

U.S. Pat. No. 3,934,004 to Orren does not specifically disclose antiperspirant stick compositions, does not disclose clear antiperspirant stick compositions, and does not disclose that the reducing agent has an effect on, e.g., stability of the stick composition over extended periods of time.

U.S. Pat. No. 4,246,285 to Van Duzee discloses skin conditioning compositions, in the form of lotions, creams, solutions, gels and solids, containing guanidine inorganic salts, the compositions consisting essentially of the guanidine inorganic salts and a cosmetically acceptable vehicle capable of delivering the guanidine to the skin. This patent discloses that the guanidine inorganic salt, which can be guanidine carbonate, guanidine hydrochloride, guanidine bisulfite, guanidine sulfate, guanidine phosphate and/or guanidine hydrobromide, provides a skin conditioning benefit.

U.S. Pat. No. 4,246,285 does not disclose any effect of the guanidine compounds on stability of the disclosed skin conditioning compositions including the solid-form compositions. This patent is not concerned with an antiperspirant gel stick composition, or such composition that is clear.

Accordingly, it is still desired to provide stable, clear, antiperspirant solid gel stick compositions, containing an acidic astringent (antiperspirant) active and gelled with dibenzylidene sorbitol, which is stable over extended periods of time, and wherein the dibenzylidene sorbitol gelling agent does not deteriorate over extended periods of time.

SUMMARY OF THE INVENTION

Accordingly, it is an object of the present invention to provide a clear, antiperspirant material-containing (in particular, an acidic, antiperspirant, astringent metal salt-containing), gel stick composition, containing dibenzylidene sorbitol as gelling agent, that is stable over extended periods of time, and methods of manufacturing such gel stick compositions.

It is a further object of the present invention to provide a clear antiperspirant solid gel stick composition, containing an antiperspirant active (in particular, an acidic antiperspirant active), and dibenzylidene sorbitol as a gelling agent, that is stable over extended periods of time.

It is a further object of the present invention to provide a clear antiperspirant solid gel stick composition, containing an antiperspirant active salt and gelled by dibenzylidene sorbitol, the stick having structural integrity over extended periods of time (that is, to provide a rigid solid stick maintaining rigidity over extended periods of time).

It is a further objection of the present invention to provide a clear antiperspirant stick composition, containing an acidic antiperspirant active ingredient and gelled by a dibenzylidene sorbitol gelling agent, the gel and gelling agent being stabilized over time against deterioration, and wherein production of benzaldehydes and formaldehydes therefrom is minimized.

It is a still further object of the present invention to provide a clear antiperspirant solid gel stick composition, having an acidic antiperspirant active (such as an astringent metallic salt, e.g., an astringent aluminum salt), and gelled by dibenzylidene sorbitol, yet wherein the dibenzylidene sorbitol is stabilized against deterioration over extended periods of time.

It is a still further object of the present invention to provide a method of manufacturing clear antiperspirant solid gel stick compositions, utilizing dibenzylidene sorbitol as a gelling agent, wherein the processing for forming the stick is simplified.

It is a further object of the present invention to provide a method of manufacturing a clear antiperspirant solid gel stick, containing an acidic antiperspirant active and gelled with dibenzylidene sorbitol, wherein degradation of the dibenzylidene sorbitol, and formation of benzaldehydes and formaldehydes, are minimized.

It is a further object of the present invention to provide a method of manufacturing clear antiperspirant sticks, containing an acidic antiperspirant active and gelled with dibenzylidene sorbitol, wherein the gelling agent and antiperspirant active are kept separate until late in the manufacturing process, so as to minimize degradation of the dibenzylidene sorbitol.

It is a further object of the present invention to provide a method of manufacturing clear antiperspirant stick composition, containing an acidic antiperspirant active ingredient and with dibenzylidene sorbitol as a gelling agent, wherein the composition can be formed continuously.

Various of the foregoing objects are achieved according to the present invention, by using a guanidine compound, or mixture of guanidine compounds, as a stabilizing agent for the antiperspirant stick composition (e.g., clear antiperspirant solid gel stick composition). The composition according to the present invention includes (but, of course, is not limited to) the antiperspirant active ingredient (for example, an acidic antiperspirant active ingredient, such as an astringent metallic salt, including astringent aluminum salts), dibenzylidene sorbitol, at least one solvent for the dibenzylidene sorbitol, and at least one guanidine compound. As can be appreciated by one of ordinary skill in the art, the composition according to the present invention can include components conventionally in antiperspirant stick compositions, including (but not limited to) emollients, detackifying agents, perfumes (fragrances), antibacterial agents, etc.

Illustrative guanidine compounds that can be incorporated in the antiperspirant stick compositions according to the present invention include guanidine carbonate, aminoguanidine bicarbonate, guanidine phosphate, guanidine hydrochloride (guanidine HCL), guanidine nitrate, guanidine sulfonate, other guanidine compounds such as guanidine bisulfite and guanidine hydrobromide, and mixtures thereof. Preferred guanidine compounds include aminoguanidine bicarbonate and guanidine carbonate, and mixtures thereof; these two compounds easily go into solution in the manufacture of the stick composition, and, accordingly, facilitate the manufacture of the clear antiperspirant stick.

Various objects of the present invention are also achieved by a method wherein a gelling agent phase, containing dibenzylidene sorbitol, and an active phase, containing the antiperspirant active ingredient (for example, antiperspirant active metal salt), are kept separate until just prior to filling the composition into dispensing containers. A high speed disperser mixer is utilized to mix ingredients (other than those in the active phase) including the gelling agent and guanidine compound, to form the gelling agent phase; and the gelling agent phase and the antiperspirant active phase are then blended and mixed using a multiple head metering pump system, prior to cooling to form the gel product.

More specifically, multiple ingredient streams are continuously blended to produce a clear antiperspirant product. A dibenzylidene sorbitol gelling agent stream is combined with the active ingredient stream and, e.g., a detackifier/fragrance/color stream, continuously, to produce the complete composition. All of the streams are combined at one time via a multiple head metering pump just prior to filling the dispensing container; accordingly, degradation of the dibenzylidene sorbitol in the finished composition is minimized.

This aspect of the present invention, which uses continuous blending of ingredients, has advantages over batch processing. In the batch processing, the combination of all ingredients results in an unstable batch in which the dibenzylidene sorbitol degrades over time. Moreover, separation of gelling agent and active ingredient into separate streams, until late in the manufacturing process, as in the present invention, allows for a most stable product, and avoids holding combined ingredients together.

Various of the foregoing objects are further achieved by a continuous processing of the components of the stick composition, using a twin-screw extruder. The dry and liquid ingredients are transferred to the twin-screw extruder, combined, and heated or cooled to form the finished product continuously. The benzylidene sorbitol gelling agent and guanidine compound are combined prior to combining the antiperspirant active material with the benzylidene sorbitol gelling agent. An extremely short contact time of the dibenzylidene sorbitol gelling agent and the antiperspirant active ingredient is used, producing a firm product with minimal degradation of the dibenzylidene sorbitol. Moreover, by rapidly combining the dibenzylidene sorbitol gelling agent and active ingredient, using the twin-screw extruder, degradation of the gelling agent is minimized.

By using the twin-screw extruder, raw materials can be fed into the extruder in dry form, and/or at room temperature. The dibenzylidene sorbitol and active ingredient contact for a minimal time prior to filling a dispensing container, resulting in a firm product with little degradation of dibenzylidene sorbitol into benzaldehydes and formaldehydes. Moreover, a stable finished product is provided.

By incorporating the guanidine compounds, as a stabilizer, in the stick composition gelled with dibenzylidene sorbitol and containing the antiperspirant active material (e.g., an acidic antiperspirant metallic salt), the composition is stabilized against deterioration, including deterioration of the gelling agent, for extended periods of time, and there is reduced formation of benzaldehyde and formaldehydes. Moreover, the stick produced can be clear and can be a rigid solid, with good structural integrity.

Furthermore, the guanidine compound (for example, guanidine carbonate and/or aminoguanidine bicarbonate) can easily be dissolved in the dibenzylidene sorbitol phase, facilitating the manufacturing process. In addition, by holding the gelling agent phase and antiperspirant active ingredient phase separately, and using a high speed dispersing mixer and multiple head metering pump, degradation of the dibenzylidene sorbitol is minimized. Furthermore, by using a twin-screw extruder, the product can be formed in a continuous procedure, with limited degradation of the dibenzylidene sorbitol.

DETAILED DESCRIPTION OF THE INVENTION

While the invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Throughout the present specification, where compositions are described as including or comprising specific components, it is contemplated by the inventors that compositions of the present invention also consist essentially of, or consist of, the recited components. Accordingly, throughout the disclosure any described composition can consist essentially of, or consist of, the recited components.

The term "clear" is used herein in its usual dictionary definition. That is, a clear antiperspirant stick, like glass, allows for ready viewing of objects behind it. By contrast, a translucent antiperspirant stick, although allowing light to pass throughout it, causes the light to scatter, making it impossible to clearly identify objects behind it.

The present invention contemplates a clear, antiperspirant stick composition, containing an antiperspirant active ingredient, dibenzylidene sorbitol as a gelling agent, and a solvent for the dibenzylidene sorbitol, and also including guanidine compounds as stabilizing agents for the stick composition. The guanidine compounds reduce deterioration of the stick composition both during manufacture and over extended periods of time of the product life, reducing degradation of the dibenzylidene sorbitol gelling agent and minimizing production of benzaldehydes and formaldehydes (and, correspondingly, minimizing odors and reduction in clarity due to such benzaldehydes and such formaldehydes). Moreover, the guanidine compounds, particularly guanidine carbonate and aminoguanidine bicarbonate, can easily go into solution in formation of the antiperspirant stick, which facilitates manufacture of the clear stick.

A first component of the compositions according to the present invention is the antiperspirant active material. Various antiperspirant active materials that can be utilized according to the present invention include conventional aluminum and aluminum/zirconium salts, as well as aluminum/zirconium salts complexed with a neutral amino acid such as glycine, as known in the art. See each of EPA No. 512,770A1 and PCT No. WO92/19221, the contents of each of which are incorporated herein by reference in their entirety, for disclosure of antiperspirant active materials. The antiperspirant active materials disclosed therein, including the acidic antiperspirant materials, can be incorporated in the compositions of the present invention. These materials include (but are not limited to) aluminum chlorohydroxide, aluminum chloride, aluminum sesquichlorohydroxide, zirconyl hydroxychloride, and aluminum chlorohydrol-propylene glycol complex. The antiperspirant actives that can be incorporated in the compositions of the present invention include the enhanced efficacy aluminum salts and the enhanced efficacy zirconium/aluminum salt-glycine materials, having enhanced efficacy due to improved molecular distribution, known in the art and discussed, e.g., in PCT No. WO92/19221, the contents of which have previously been incorporated by reference in their entirety herein.

The amount of antiperspirant active material incorporated in the stick composition of the present invention is, preferably, an antiperspirant effective amount; that is, an amount to reduce the flow of perspiration from the location (for example, axillary region of a human) to which the antiperspirant is applied. Illustratively, but not limiting, the antiperspirant active material is incorporated in the composition in an amount of from about 0.5% by weight to about 35% by weight, preferably from about 5% to about 35% by weight, of the total weight of the composition. The amount of antiperspirant material utilized is dependent on the efficacy of the specific antiperspirant material, as well as a maximum amount which avoids a reduction in clarity of the final product.

The antiperspirant stick compositions according to the present invention include a solvent, employed to solubilize at least the gelling agent. The solvent forms the base matrix of the solid stick when combined with the gelling agent. The solvent desirably also solubilizes the antiperspirant active, to form a clear product, and can also solubilize other components, in order to produce miscible products which can be formed into transparent gels. Various solvents which can be utilized according to the present invention are disclosed in EPA No. 512,770A1 and PCT No. WO92/19221, each of which has previously been incorporated by reference in their entirety in the present application. Such solvents include (and are not limited to) dihydroxy aliphatic alcohols containing from 3 to 6 carbon atoms, such as 1,3-propylene glycol, 1,2-propylene glycol, 1,3-butylene glycol, 1,4-butylene glycol and hexylene glycol; and various liquid polyethylene and polypropylene glycols, monohydric alcohols such as ethanol, n-propanol, etc. The solvents are also described, for example, in U.S. Pat. No. 4,518,582, the contents of which are incorporated herein by reference in their entirety. Particularly preferred solvents include propylene glycol, dipropylene glycol, butylene glycol, hexylene glycol, PPG-10 butanediol, and mixtures thereof.

The solvent (or solvents) is utilized as a solvent for the gelling agent and preferably as a solvent for the antiperspirant active material, to form a clear product, and forms the base matrix of the solid stick when combined with the gelling agent. Preferably, the solvent (or solvents) is included in the composition in amounts of, for example, 5–98%, preferably 7–90%, most preferably 60–85%, by weight, of the total weight of the composition.

The gelling agent incorporated in the composition of the present invention is a dibenzylidene sorbitol, or derivative thereof. In the present disclosure, reference to dibenzylidene sorbitol includes derivatives of dibenzylidene sorbitol which can be used as gelling agents for solid gel stick compositions containing antiperspirant active materials according to the present invention. The dibenzylidene sorbitol gelling agents and derivatives thereof are described in PCT No. WO92/19221, the contents of which have been incorporated herein by reference in their entirety.

Generally, an amount of gelling agent utilized in the composition of the present invention is an amount sufficient to gel the composition. Illustratively, the amount of gelling agent included in the composition can be about 0.5% to about 10%, preferably from about 2% to about 5%, most preferably from about 2% to about 3.5%, by weight, of the total weight of the composition.

A preferred gelling agent to be incorporated in the composition of the present invention is "MILLITHIX 925", manufactured by Milliken Chemical, a division of Milliken & Company.

An essential component of the present invention is the guanidine compound, which acts as a stabilizer for the present composition. Various guanidine compounds which can be utilized according to the present invention have been discussed previously. These compounds are strongly basic compounds. Preferred guanidine compounds include guanidine carbonate and/or aminoguanidine bicarbonate, each of which easily forms solutions with the gelling agent in the solvent of the present invention.

Guanidine carbonate, which has a $pK_b$ of 2.76 (this compound is a strongly basic compound, being an alkaline salt of guanidine) is a white to slightly yellowish crystalline powder, having a melting point of 197° C. and a density of 1.3 $g/cm^3$.

The guanidine compound is incorporated in the antiperspirant stick compositions of the present invention in amounts sufficient to stabilize the composition (that is, prevent degradation of the composition during manufacture of the composition and over extended periods of time thereafter). Illustratively, the guanidine compound is included in the composition in an amount of 0.1% to 3% by weight, of the total weight of the composition. A preferred range for the guanidine compound is 0.25% by weight to 1.25% by weight, of the total weight of the composition.

The compositions of the present invention can include various known detackifying agents and emollients. Such detackifiers and emollients are disclosed in EPA No. 512,770A1 and PCT No. WO92/19221, the contents of each of which has been previously incorporated herein by reference in their entirety. These agents and emollients prevent stickiness of the compositions after they have dried on the skin surface, and enhance the feel of the compositions and the ease with which they can be applied. Illustrative amounts of the detackifiers and emollients are disclosed in EPA No. 512,770A1 and PCT No. WO92/19221, and include (but are not limited to) 1%–40% by weight, of the total weight of the composition, of one or more emollients and/or detackifiers.

The compositions according to the present invention can also include other, optional, components conventionally incorporated in antiperspirant stick compositions, including (but not limited to) perfumes (fragrances), antibacterial agents, fungistats, pigments, dyes, colorants, ultraviolet absorbers, etc. Illustratively, and not limiting, the perfumes normally employed in cosmetic compositions can be employed in compositions of the present invention, if desired, with concentrations of such perfumes typically being up to about 2%, e.g., about 0.5% to 2%, by weight, of the total weight of the composition.

An illustrative antibacterial agent that can be utilized according to the present invention is Triclosan; typically, compositions according to the present invention may contain up to about 2% antibacterial agents, preferably about 0.1% to 1.5%, by weight, of the total weight of the composition. Other antibacterial agents that can be utilized according to the present invention include benzethonium chloride and zinc phenolsulfonate.

Compositions according to the present invention are preferably anhydrous, although they can contain small amounts (e.g., up to 5% by weight, of the total weight of the composition) of water.

The present invention also includes processes of making the antiperspirant solid gel stick composition, so as to reduce degradation of the stick composition during manufacture thereof and minimize production of benzaldehydes and formaldehydes. In the following, two separate processes achieving the objectives of the present invention will be discussed, forming a clear antiperspirant solid gel stick composition of the following formula (where all percentages are percent by weight, of the total weight of the composition):

| COMPOSITION I | |
|---|---|
| Rezal 36 GPG (30% soln of antiperspirant active in propylene glycol) | 44.70% |
| Propylene Glycol USP (in addition to the solvent in Rezal 36 GPG) | 31.52% |
| PEG-6 (Carbowax 300) | 5.00% |
| Benzylidene Sorbitol (Millithix 925) | 2.50% |
| Guanidine Carbonate | 0.70% |
| PPG-10 Butanediol (Probutyl DB-10) | 8.00% |
| DC 2501 wax | 2.00% |
| Diisopropyl Sebacate (Unimate DIPS) | 2.00% |
| $C_{12}$–$C_{15}$ Alkyl Lactate (Ceraphyl 41) | 2.00% |
| Silica | 0.50% |
| Fragrance | 1.00% |
| Color Solution | 0.08% |
| TOTAL | 100.00% |

Figure 1:
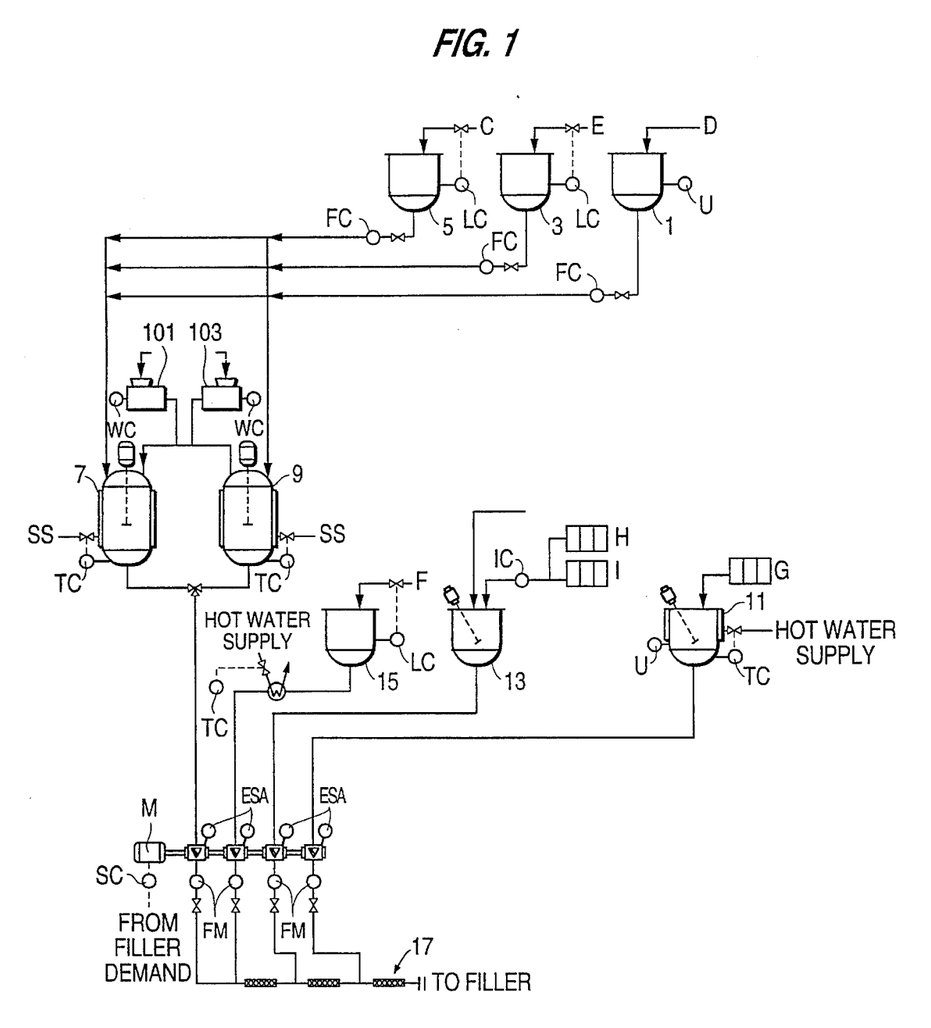
FIG. 1 is a flow diagram of a first process for forming the clear antiperspirant stick composition of the present invention.

The first process will be discussed in connection with FIG. 1, which is a flow diagram of a first process for forming the clear antiperspirant stick composition of the present invention, by, e.g., a batch blending process.

Initially, liquid propylene glycol (from tank 1), liquid Carbowax 300 (from tank 3) and liquid Probutyl DB-10 (from tank 5 are passed via pumps into a high speed disperser mixer or equivalent (either tank 7 or tank 9). The combined liquids are then heated, for example, to 115° C., under a nitrogen gas blanket; and then the gelling agent ("MILLITHIX 925") powder, guanidine carbonate powder, and silica powder are added via gravimetric loss-in-weight feeders (e.g., represented by reference characters 101 and 103). Illustratively, the gelling agent and guanidine carbonate powder can be added from one of the feeders, while the silica powder can be added via the other feeder, into the high speed disperser mixer. The high speed disperser mixer is operated for, for example, 5–10 minutes to mix the powders and liquids, until all powders are solubilized. The solution is then held at 105°–110° C. for a maximum of four hours. Tanks 7 and 9 can be used in rotation, for example.

In tank 15, the liquid Rezal 36 GPG (30% solution) antiperspirant active ingredient is held at ambient temperature.

In tank 13, the liquid Unimate DIPS, liquid Ceraphyl 41, liquid fragrance and liquid color solutions are mixed and held at ambient temperature.

In tank 11, the solid DC 2501 wax is liquified, and held at 35° C. DC 2501 can also be added directly into tank 15 and the contents then mixed and held at 35° C.

Thereafter, four liquid streams, from tanks 7 or 9, from tank 15, from tank 13 and from tank 11, are continuously blended to make a finished product, utilizing a multiple head metering pump. The streams are pumped, illustratively, at flow rates as shown in the following Table 1:

TABLE 1

|  | Temperature | Flow Rate % |
|---|---|---|
| Stream 1 from Tank 7 or 9 | 105°–110° C. | 48.22 |
| Stream 6 from Tank 15 | 65° C. (from heat exch) | 44.70 |
| Stream 7 from Tank 13 | 25° C. (ambient) | 5.08 |
| Stream 8 from Tank 11 | 35° C. | 2.00 |

The combined stream is mixed, e.g., via a static mixer, and then is pumped to a filler, where dispensing containers are filled as is known in the art, and the composition cooled to form solid gel sticks.

Figure 2:
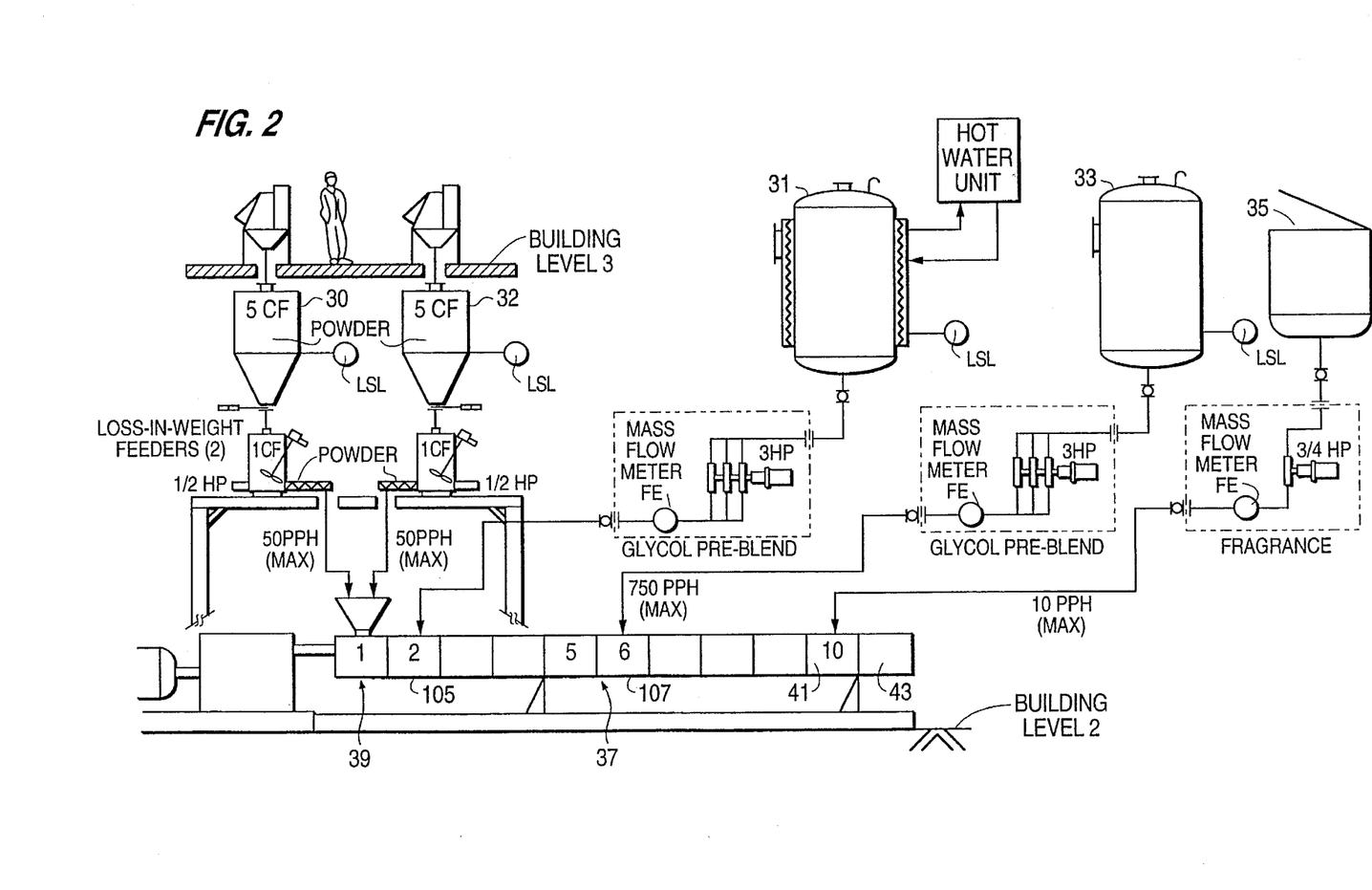
FIG. 2 is a flow diagram of a second process for forming the clear antiperspirant stick composition of the present invention.

A second process, which is also a continuous process for forming the clear antiperspirant solid gel sticks, according to the present invention, will be described in connection with FIG. 2. The second process utilizes a twin-screw extruder, such as a twin-screw, continuous processing extruder, for processing health care and pharmaceutical products, such as manufactured by Werner & Pfleiderer Corporation. The twin-screw, continuous processing extruder manufactured by Werner & Pfleiderer Corporation is illustrative of an extruder useful for the present invention, and is not limiting of the present invention.

Initially, a blend of "MILLITHIX 925" gelling agent and guanidine carbonate is loaded into a gravimetric loss-in-weight feeder 30, and held at ambient temperature. In a second hopper, the silica powder is loaded into a gravimetric loss-in-weight feeder 32 and held at ambient temperature.

In a first tank 31, liquid propylene glycol, liquid Carbowax 300, and Probutyl DB-10 are mixed and held at ambient temperature. In a second tank 33, liquid Rezal 36 GPG (30% solution) is held in a tank at ambient temperature to 35° C., and liquified DC 2501 wax is added and mixed with low agitation. In tank 35, liquid Unimate DIPS, liquid Ceraphyl 41, liquid fragrance and liquid color solutions are mixed and held at ambient temperature.

Thereafter, the ingredient streams from the two hoppers and from tanks 31, 33 and 35 are continuously delivered into the twin-screw extruder 37. The "MILLITHIX 925" and guanidine carbonate are entered into a first barrel 39 of the extruder, and the propylene glycol/Carbowax 300/Probutyl DB-10 is delivered to the extruder in a second barrel 105 of the extruder block and instantly heated to 115°–120° C. by temperature controls on the extruder block. The mixture is extruded through barrels 2 to 5 and cooled to 100° C. At barrel 6, referred to by reference character 107 in FIG. 2, Rezal 36 GPG/DC 2501 is added from Tank 33, and the combined mixture is extruded and cooled to 90° C. by barrel 9 of the extruder. At barrel 10 of the extruder, referred to by reference character 41, Unimate DIPS/Ceraphyl 41/fragrance/color solution is added and extruded through the remaining barrel of the extruder. Product discharges from the extruder at the eleventh barrel thereof (referred to by reference character 43). The product then is transferred to a conventional filler apparatus, to fill dispensing containers as done conventionally. Illustratively, the product residence time from raw material to finished product, in the extruder, is less than 4 minutes on a pilot scale unit.

Flow rates from each of the hoppers, and from the three tanks 31, 33 and 35, are shown in the following Table 2:

TABLE 2

| Ingredient Stream | Continuous Flow Rate % |
|---|---|
| Millithix 925/guanidine carbonate | 3.20% |
| Silica | 0.50% |
| Propylene glycol/Carbowax 300/Probutyl DB10 | 44.52% |
| Rezal 356 GPG (30% soln)/DC 2501 | 46.70% |
| Unimate DIPS/Ceraphyl 41/Fragrance/ Colors | 05.08% |
| TOTAL | 100.00 |

Alternatively, the DC 2501 (wax) can be added separately, rather than together with the active antiperspirant agent. Moreover, the active antiperspirant agent can be added into the eight barrel, at ambient temperature, with the combined stream in the extruder having been cooled to 100° C. by the eight barrel.

According to this aspect of the present invention, a dry blend can be initially fed to the extruder, and then a solvent phase added. Thereafter, the active ingredient and then the fragrance can be added.

As seen in the foregoing, continuous processing can be utilized, with the gelling agent and active ingredient being kept separate until relatively late in the processing sequence. Moreover, the guanidine compound is present when the dibenzylidene sorbitol gelling agent and the antiperspirant active material are combined. Accordingly, degradation of the dibenzylidene sorbitol gelling agent can be minimized.

The antiperspirant solid gel stick composition according to the present invention is used as such stick compositions are conventionally used. Specifically, the composition can be filled into a dispensing container as done conventionally, with the composition hardening in such container. The composition is used by elevating and exposing the stick out of the dispensing container, as done conventionally, and applying the product to, e.g., axillary regions of the body, so as to provide antiperspirant protection.

In the following are disclosed various compositions according to the present invention. These compositions contain guanidine compounds as stabilizers. In the following examples, which are illustrative and not limiting, as well as throughout the rest of this disclosure, the names of the components are names as in the *CTFA International Cosmetic Ingredient Dictionary* (4th Ed. 1991), and amounts are percent by weight, of the total weight of the composition.

| Ingredients: | Example 1 | Example 2 |
|---|---|---|
| Aluminum-zirconium Tetrachlorohydrex Gly-PG (30% soln. of active material in propylene glycol | 44.70 | 44.70 |
| Propylene Glycol (in addition to that used as solvent for the antiperspirant active) | 51.80 | 49.80 |
| Dibenzylidene Sorbitol | 2.50 | 2.50 |
| Guanidine Carbonate | 1.00 | 3.00 |
| TOTAL | 100.00 | 100.00 |

In both Examples 1 and 2, the solidified gel stick is clear, showing that a clear antiperspirant solid gel stick can be provided where the amount of guanidine compound incorporated in the stick is up to 3% by weight, of the total weight of the composition.

EXAMPLES 3–5

The following examples show stick compositions containing varying amounts of guanidine carbonate.

| Ingredients | Example 3 | Example 4 | Example 5 |
|---|---|---|---|
| PPG-10 Butanediol | 12.3 | 12.3 | 12.3 |
| 1,6-Hexanediol | 0.5 | 0.5 | 0.5 |
| Isoprene Glycol | 2.0 | 2.0 | 2.0 |
| PEG-4 | 5.0 | 5.0 | 5.0 |
| Dipropylene Glycol | 10.0 | 10.0 | 10.0 |
| Propylene Glycol | 11.88 | 12.13 | 12.38 |
| Dimethicone Copolyol | 4.0 | 4.0 | 4.0 |
| Dibenzylidene Sorbitol | 2.5 | 2.5 | 2.5 |
| Guanidine Carbonate | 0.75 | 0.5 | 0.25 |
| Rezal 36 GPG (30%) | 50.0 | 50.0 | 50.0 |
| Fragrance | 1.0 | 1.0 | 1.0 |
| Color | 0.07 | 0.07 | 0.07 |

EXAMPLES 6–11

The following examples show antiperspirant stick compositions with aminoguanidine bicarbonate as the stabilizing compound, and various solvents for the dibenzylidene sorbitol gelling agent.

| | Example 6 | Example 7 | Example 8 | Example 9 | Example 10 | Example 11 |
|---|---|---|---|---|---|---|
| 1. Al—Zr Tetrachlorohydrex GLY-PG (30%) | 44.7% | 44.7% | 44.7% | 44.7% | 44.7% | 44.7% |
| 2. Dibenzylidene Sorbitol | 2.5% | 2.5% | 2.5% | 2.5% | 2.5% | 2.5% |
| 3. Aminoguanidine Bicarbonate | 1.5% | 1.5% | 1.5% | 1.5% | 1.5% | 1.5% |
| 4. Propylene Glycol | 51.3% | | | | | |
| 5. Dipropylene Glycol | | 51.3% | | | | |
| 6. Butylene Glycol | | | 51.3% | | | |
| 7. PEG 4 | | | | 51.3% | | |
| 8. PEG 6 | | | | | 51.3% | |
| 9. PEG 8 | | | | | | 51.3% |
| TOTAL | 100.0 | 100.0 | 100.0 | 100.0 | 100.0 | 100.0 |

The resulting products of each of Examples 6–11 are sufficiently clear for commercial purposes. These examples show that aminoguanidine carbonate is a satisfactory stabilizer for gel stick compositions containing various solvents.

EXAMPLES 12–14

The following Examples 12–14 show various amounts of aminoguanidine bicarbonate incorporated in clear antiperspirant solid gel sticks, with dibenzylidene sorbitol as the gelling agent.

| INGREDIENTS | Example 12 | Example 13 | Example 14 |
|---|---|---|---|
| 1. Al—Zr Tetrachlorohydrex-GLY-PG (30%) | 44.7% | 47.7% | 47.7% |
| 2. Dibenzylidene Sorbitol | 2.5% | 2.5% | 2.5% |
| 3. Amino Guanidine Bicarbonate | 1.0% | 1.5% | 2.0% |
| 4. Propylene Glycol | 51.8% | 51.3% | 50.8% |
| TOTAL | 100.0 | 100.0 | 100.0 |

EXAMPLES 15–18

The following Examples 15–18 illustrate various compositions wherein the amount of diisopropyl sebacate is varied, while still forming clear antiperspirant solid gel sticks. In each of these Examples 15–18, the compositions were formed by the following steps:

1. Heat Rezal 36 GPG (30% solution) to 80° C.
2. Mix the propylene glycol, dipropylene glycol, PEG-6, and PPG-10 butanediol, and heat to 90° C.
3. At 90° C., add the guanidine carbonate and continue heating to 120° C.
4. At 120° C., add the dibenzylidene sorbitol, and mix until a clear solution results.
5. Upon achieving a clear solution, add the diisopropyl sebacate and mix briefly.
6. Add the resulting phase from 5 to the active phase of step 1, and cool to 90° C.
7. At 90° C., add the fragrance and cool to 85° C.
8. At 85° C., pour into stick containers.

| Ingredients | % |
|---|---|
| EXAMPLE 15 | |
| Rezal 36 GPG (30% soln) | 44.7 |
| Propylene Glycol | 32.1 |
| PEG-6 | 5.0 |
| Dipropylene Glycol | 5.0 |
| PPG-10 Butamediol | 8.0 |
| Guanidine Carbonate | 0.7 |
| Dibenzylidene Sorbitol | 2.5 |
| Diisopropyl Sebacate | 1.0 |
| Fragrance | 1.0 |
| TOTAL | 100.0 |
| EXAMPLE 16 | |
| Rezal 36 GPG (30% soln) | 44.7 |

| Ingredients | % |
|---|---|
| Propylene Glycol | 32.1 |
| PEG-6 | 5.0 |
| Dipropylene Glycol | 4.0 |
| PPG-10 Butanediol | 8.0 |
| Guanidine Carbonate | 0.7 |
| Dibenzylidene Sorbitol | 2.5 |
| Diisopropyl Sebacate | 2.0 |
| Fragrance | 1.0 |
| TOTAL | 100.0 |

EXAMPLE 17

| Ingredients | % |
|---|---|
| Rezal 36 GPG (30% soln) | 44.7 |
| Propylene Glycol | 32.1 |
| PEG-6 | 5.0 |
| Dipropylene Glycol | 3.0 |
| PPG-10 Butanediol | 8.0 |
| Guanidine carbonate | 0.7 |
| Dibenzylidene Sorbitol | 2.5 |
| Diisopropyl Sebacate | 3.0 |
| Fragrance | 1.0 |
| TOTAL | 100.0 |

EXAMPLE 18

| Ingredients | % |
|---|---|
| Rezal 36 GPG (30% soln) | 44.7 |
| Propylene Glycol | 32.1 |
| PEG-6 | 5.0 |
| Dipropylene Glycol | 2.0 |
| PPG-10 Butanediol | 8.0 |
| Guanidine Carbonate | 0.7 |
| Dibenzylidene Sorbitol | 2.5 |
| Diisopropyl Sebacate | 4.0 |
| Fragrance | 1.0 |
| TOTAL | 100.0 |

EXAMPLES 19–23

The following Examples 19–23 show various clear antiperspirant solid gel stick compositions wherein the amount of Ceraphyl 41 ($C_{12}$–$C_{15}$ alkyl lactate), as a detackifier, is varied. The procedure utilized for forming these Examples 19–23 is the same as utilized in forming the compositions of Examples 15–18 and set forth previously, with $C_{12}$–$C_{15}$ alkyl lactate substituted for the diisopropyl sebacate in the processing steps.

| Ingredients | % |
|---|---|
| EXAMPLE 19 | |
| Rezal 36 GPG (30% soln) | 44.7 |
| Propylene Glycol | 32.1 |
| PEG-6 | 5.0 |
| Dipropylene Glycol | 5.0 |
| PPG-10 Butanediol | 8.0 |
| Guanidine Carbonate | 0.7 |
| Dibenzylidene Sorbitol | 2.5 |
| Ceraphyl 41 (C12–C15 Alkyl lactate) | 1.0 |
| Fragrance | 1.0 |
| TOTAL | 100.0 |
| EXAMPLE 20 | |
| Rezal 36 GPG (30% soln) | 44.7 |
| Propylene Glycol | 32.1 |
| PEG-6 | 5.0 |
| Dipropylene Glycol | 4.0 |
| PPG-10 Butanediol | 5.0 |
| Guanidine Carbonate | 0.7 |
| Dibenzylidene Sorbitol | 2.5 |
| Ceraphyl 41 | 2.0 |
| Fragrance | 1.0 |
| TOTAL | 100.0 |
| EXAMPLE 21 | |
| Rezal 36 GPG (30% soln) | 44.7 |
| Propylene Glycol | 32.1 |
| PEG-6 | 5.0 |
| Dipropylene Glycol | 3.0 |
| PPG-10 Butanediol | 8.0 |
| Guanidine Carbonate | 0.7 |
| Dibenzylidene Sorbitol | 2.5 |
| Ceraphyl 41 | 3.0 |
| Fragrance | 1.0 |
| TOTAL | 100.0 |
| EXAMPLE 22 | |
| Rezal 36 GPG (30% soln) | 44.7 |
| Propylene Glycol | 32.1 |
| PEG-6 | 5.0 |
| Dipropylene Glycol | 2.0 |
| PPG-10 Butanediol | 8.0 |
| Guanidine Carbonate | 0.7 |
| Dibenzylidene Sorbitol | 2.5 |
| Ceraphyl 41 | 4.0 |
| Fragrance | 1.0 |
| TOTAL | 100.0 |
| EXAMPLE 23 | |
| Rezal 36 GPG (30% soln) | 44.7 |
| Propylene Glycol | 32.1 |
| PEG-6 | 5.0 |
| PPG-10 Butanediol | 8.0 |
| Guanidine Carbonate | 0.7 |
| Dibenzylidene Sorbitol | 2.5 |
| Ceraphyl 41 | 6.0 |
| Fragrance | 1.0 |
| TOTAL | 100.0 |

Example 24 shows a further embodiment of an antiperspirant solid gel stick composition, within the scope of the present invention.

| Ingredients | % |
|---|---|
| Al—Zr Tetrachlorohydrex GLY-PG (30%) | 44.70 |
| Propylene Glycol | 31.52 |
| PPG-10 Butanediol | 8.00 |
| PEG-6 | 5.0 |
| Dibenzylidene Sorbitol | 2.50 |
| Diisopropyl Sebacate | 2.00 |
| C12–C15 Alkyl Lactate | 2.00 |
| Dimethicone Copolyol | 2.00 |
| Guanidine Carbonate | 0.70 |
| Silica | 0.50 |
| Fragrance | 1.00 |
| Color | Q.S. |
| TOTAL | 100.0 |

Accordingly, by the present invention, a clear antiperspirant solid gel stick that maintains stability over extended periods of time, and wherein the dibenzylidene sorbitol gelling agent is not degraded even when an acidic antiperspirant active is utilized, is achieved. Moreover, by using the processing of the present invention, a clear antiperspirant solid gel stick having reduced degradation of the stick composition, including the dibenzylidene sorbitol, during manufacture of the stick, is achieved.

While we have shown and described several embodiments in accordance with the present invention, it is understood that the same is not limited thereto, but is susceptible to numerous changes and modifications as known to one having ordinary skill in the art, and we therefore do not wish to be limited to the details shown and described herein, but intend to cover all such modifications as are encompassed by the scope of the appended claims.

We claim:

1. A clear, antiperspirant metal salt-containing, gel stick composition, comprising:
   a) an antiperspirant metal salt, in an antiperspirant effective amount;
   b) dibenzylidene sorbitol as a gelling agent, in an amount sufficient to form a gel of the composition;
   c) a solvent for the dibenzylidene sorbitol, in an amount sufficient to dissolve all of the dibenzylidene sorbitol; and
   d) a guanidine compound, wherein said guanidine compound is selected from the group consisting of guanidine carbonate, aminoguanidine bicarbonate, guanidine phosphate, guanidine hydrochloride, guanidine nitrate, guanidine sulfonate, guanidine bisulfate and guanidine hydrobromide, and mixtures thereof, said guanidine compound being in the composition in an amount sufficient to stabilize the gel stick composition.

2. The composition according to claim 1, wherein the antiperspirant metal salt is included in the composition in an amount sufficient to reduce perspiration when applied to axillary regions of a human.

3. The composition according to claim 1, wherein the antiperspirant metal salt is dissolved in the composition.

4. The composition according to claim 3, wherein the antiperspirant metal salt includes an acidic astringent metallic salt.

5. The composition according to claim 3, wherein the antiperspirant metal salt is included in the composition in an amount sufficient to reduce perspiration when applied to axillary regions of a human.

6. The composition according to claim 1, wherein the guanidine compound includes guanidine carbonate.

7. The composition according to claim 1, wherein the guanidine compound includes aminoguanidine bicarbonate.

8. The composition according to claim 1, wherein the guanidine compound is included in the composition in an amount of 0.1% to 3% by weight, of the total weight of the composition.

9. The composition according to claim 8, wherein the guanidine compound is included in the composition in an amount of 0.25% to 1.25% by weight, of the total weight of the composition.

10. The composition according to claim 8, wherein the solvent includes polyhydric alcohol.

11. The composition according to claim 8, wherein the solvent includes at least one of propylene glycol, butylene glycol, dipropylene glycol and hexylene glycol.

12. The composition according to claim 10, wherein the composition includes the antiperspirant metal salt in an amount of 0.5%–35% by weight, includes the solvent in an amount of 5%–98% by weight, and includes the dibenzylidene sorbitol in an amount of 0.5%–10% by weight, of the total weight of the composition.

13. The composition according to claim 10, wherein the composition further includes a fragrance and an antibacterial agent.

14. The composition according to claim 1, wherein the guanidine compound is selected from the group consisting of guanidine carbonate, aminoguanidine bicarbonate, guanidine phosphate, and guanidine nitrate, and mixtures thereof.

15. The composition according to claim 14, wherein the guanidine compound is selected from the group consisting of guanidine carbonate, aminoguanidine bicarbonate and guanidine phosphate, and mixtures thereof.

16. The composition according to claim 1, wherein, of the total weight of the composition, the antiperspirant metal salt is included in the composition in an amount of 0.5–35% by weight, the dibenzylidene sorbitol is included in the composition in an amount of 0.5–10% by weight, the solvent is included in the composition in an amount of 5–98% by weight, and the guanidine compound is included in the composition in an amount of 0.1–3% by weight.

17. The composition according to claim 16, wherein said solvent is selected from the group consisting of dihydroxy aliphatic alcohols containing 3 to 6 carbon atoms, monohydric alcohols, liquid polyethylene glycols and liquid polypropylene glycols, and mixtures thereof.

18. The composition according to claim 16, wherein said solvent is selected from the group consisting of 1,3-propylene glycol, 1,2-propylene glycol, 1,3-butylene glycol, 1,4-butylene glycol, hexylene glycol, ethanol, n-propanol, dipropylene glycol, PPG-10 butanediol, and mixtures thereof.

19. The composition according to claim 1, wherein said solvent is selected from the group consisting of dihydroxy aliphatic alcohols containing 3 to 6 carbon atoms, monohydric alcohols, liquid polyethylene glycols and liquid polypropylene glycols, and mixtures thereof.

20. The composition according to claim 1, wherein said solvent is selected from the group consisting of 1,3-propylene glycol, 1,2-propylene glycol, 1,3-butylene glycol, 1,4-butylene glycol, hexylene glycol, ethanol, n-propanol, dipropylene glycol, PPG-10 butanediol and mixtures thereof.

21. The composition according to claim 1, wherein said solvent is a solvent for both the dibenzylidene sorbitol and for the antiperspirant metal salt.

22. The composition according to claim 13, wherein the antibacterial agent is selected from the group consisting of Triclosan, benzethonium chloride and zinc phenolsulfonate.

23. The composition according to claim 22, wherein the composition includes, in percent by weight of the total weight of the composition, 0.5–2% by weight fragrance and 0.1–2% by weight antibacterial agent.

24. A method of manufacturing a clear, antiperspirant metal salt-containing, gel stick composition, comprising the steps of:
   a) providing a first solution of an antiperspirant metal salt in a solvent therefor, said first solution being a liquid and containing the antiperspirant metal salt in an antiperspirant effective amount;
   b) forming a heated second solution, of (1) dibenzylidene sorbitol and (2) a guanidine compound which acts as a stabilizer for the dibenzylidene sorbitol in a solvent for the dibenzylidene sorbitol and guanidine compound, the second solution being provided by mixing solutes and the solvent in a high speed disperser mixer, the second solution being a liquid, wherein said guanidine compound is selected from the group consisting of guanidine carbonate, aminoguanidine bicarbonate, guanidine phosphate, guanidine hydrochloride, guanidine nitrate, guanidine sulfonate, guanidine bisulfate and guanidine hydrobromide, and mixtures thereof;
   c) blending and mixing the first and second solutions using a multiple heat metering pump, for a sufficiently short time such that the dibenzylidene sorbitol does not degrade and for a sufficiently long period to provide a mixture of the first and second solutions, the mixture being a liquid; and d) cooling the mixture of the first and second solutions so as to form a gel.

25. The method according to claim 24, wherein the solvent of the first solution and the solvent of the second solution each includes a polyhydric alcohol.

26. The method according to claim 25, wherein the polyhydric alcohol is propylene glycol.

27. The method according to claim 24, wherein the second solution is kept for a maximum of one hour between forming of the second solution and blending the second solution with the first solution.

28. The method according to claim 24, wherein the second solution is at a temperature of 105° C.–110° C. when blended with the first solution.

29. Product formed by the process of claim 24.

30. A method of manufacturing a clear, antiperspirant metal salt-containing, gel stick composition, comprising the steps of:

a) transferring dibenzylidene sorbitol and a guanidine compound to a twin-screw extruder, wherein said guanidine compound is selected from the group consisting of guanidine carbonate, aminoguanidine bicarbonate, guanidine phosphate, guanidine hydrochloride, guanidine nitrate, guanidine sulfonate, guanidine bisulfate and guanidine hydrobromide, and mixtures thereof;

b) transferring a solvent for the dibenzylidene sorbitol to the twin-screw extruder and heating the solvent;

c) transferring an antiperspirant metal salt to the twin-screw extruder, an amount of antiperspirant metal salt transferred being an antiperspirant effective amount in the stick composition;

d) blending and mixing the transferred materials in the twin-screw extruder, thereby forming a resulting mixture;

e) discharging the resulting mixture from the twin-screw extruder; and f) cooling the resulting mixture to form the gel stick composition.

31. The method according to claim 30, wherein steps (a), (b) and (c) are continuously performed.

32. The method according to claim 31, wherein the twin-screw extruder has a plurality of stages, in a flow direction of material through the extruder, wherein the dibenzylidene sorbitol and guanidine compound are transferred to the twin-screw extruder, in powder form, in a first stage of the twin-screw extruder; wherein the solvent for the dibenzylidene sorbitol is transferred to the twin-screw extruder in a second stage of the twin-screw extruder; and wherein the antiperspirant metal salt is transferred to the twin-screw extruder in a third stage of the twin-screw extruder.

33. The method according to claim 32, wherein the second stage is downstream of the first stage, and the third stage is downstream of the second stage, in the flow direction of material through the extruder.

34. The method according to claim 33, wherein the solvent is heated in the second stage.

35. The method according to claim 34, wherein the antiperspirant metal salt is in a solution when transferred to the twin-screw extruder.

36. The method according to claim 35, wherein the dibenzylidene sorbitol and the guanidine compound are transferred together into the twin-screw extruder, in a dry blend.

37. The method according to claim 35, wherein a solvent in which the antiperspirant metal salt is in solution, and the solvent for the dibenzylidene sorbitol, each includes propylene glycol.

38. The method according to claim 30, wherein the dibenzylidene sorbitol and the guanidine compound are transferred together into the twin-screw extruder, in a dry blend.

39. The method according to claim 30, wherein the dibenzylidene sorbitol and the guanidine compound are mixed together prior to mixing the antiperspirant metal salt with the dibenzylidene sorbitol and guanidine compound in the twin-screw extruder.

40. Product formed by the process of claim 30.

\* \* \* \* \*